(12) United States Patent
VanDeripe

(10) Patent No.: US 7,263,993 B2
(45) Date of Patent: Sep. 4, 2007

(54) METHOD OF USE OF GAS MIXTURES TO ACHIEVE WASHOUT OF NITROGEN FROM THE BODY AND MITOCHONDRIA

(76) Inventor: Donald R. VanDeripe, 1534 Woodbury Dr., St. Charles, MO (US) 63304

( * ) Notice: Subject to any disclaimer, the term of this patent is extended or adjusted under 35 U.S.C. 154(b) by 344 days.

(21) Appl. No.: 10/678,379

(22) Filed: Oct. 6, 2003

(65) Prior Publication Data

US 2004/0142044 A1    Jul. 22, 2004

Related U.S. Application Data

(63) Continuation-in-part of application No. 10/347,553, filed on Jan. 21, 2003, now abandoned.

(51) Int. Cl.
*A61M 16/00* (2006.01)
(52) U.S. Cl. .............. 128/200.24; 128/204.18
(58) Field of Classification Search ........... 128/200.24, 128/203.12, 204.18, 205.11; 424/9.3
See application file for complete search history.

(56) References Cited

U.S. PATENT DOCUMENTS

| | | | | |
|---|---|---|---|---|
| 3,688,794 | A * | 9/1972 | Bird et al. ............. | 137/529 |
| 6,001,332 | A * | 12/1999 | Garrett ................. | 424/9.3 |
| 6,536,429 | B1 * | 3/2003 | Pavlov et al. .......... | 128/203.26 |
| 6,592,848 | B1 * | 7/2003 | Lecourt ................. | 424/45 |
| 6,899,103 | B1 * | 5/2005 | Hood et al. ............. | 128/845 |
| 6,983,749 | B2 * | 1/2006 | Kumar et al. ........... | 128/204.15 |
| 2003/0106554 | A1 * | 6/2003 | de Silva et al. ........ | 128/204.22 |
| 2003/0131844 | A1 * | 7/2003 | Kumar et al. ........... | 128/200.24 |
| 2004/0234610 | A1 * | 11/2004 | Hall et al. ............. | 424/489 |
| 2006/0162725 | A1 * | 7/2006 | Downie ................. | 128/203.12 |

OTHER PUBLICATIONS

Guyton, Arthur, Textbook of Medical Physiology, W.B. Saunders Company, 6th ed., 555-556.*
Rusyniak, D. E. et. al. Hyperbaric Oxygen Therapy in acute ischemic stroke: results of the hyperbaric oxygen in acute ischemic stroke trial pilot study stroke *34* 571-574 (2003).
Marler, John R et al. Association of outcome with early stroke treatment: pooled analysis of ATLANTIS, ECASS, and NINDS rt-PA stroke trials Lancet *363* 768-774 (2004).
Donald R. Vanderipe, The swelling of mitochondria from nitrogengas; a possible cause of reperfusion damage; Medical Hypothesis *62* , p. 294-296 (2004) Elsevier.
Yi Pan et. al. Infarct Reduction by washout of inhaled nitrogen with heliox or oxygen in a rat focal ischemia model. Abstract: 59th Annual Meeting of the American Academy of Neurology—May 2007.
Piffare', R. et al. Effect of oxygen and helium mixtures on ventricular fibrillation, J. of Thoracic and Cardiovascular Surgery *60* 648-652 (1970).
Oppel, L. et al. A review of the scientific evidence on the treatment of traumatic brain injuries and stroke, with hyperbaric oxygen. Brain Injury *17* 225-236 (2003).

* cited by examiner

*Primary Examiner*—Steven O. Douglas

(57) ABSTRACT

The disclosure details methods and gas mixtures which are useful for washing nitrogen out of the body and mitochondria following acute cerebrovascular accidents (strokes) and allow the reuptake of oxygen into mitochondria of ischemic tissues following re-flow, thereby reducing the severity of reperfusion damage and cell death.

4 Claims, No Drawings

METHOD OF USE OF GAS MIXTURES TO ACHIEVE WASHOUT OF NITROGEN FROM THE BODY AND MITOCHONDRIA

CROSS REFERENCE TO RELATED APPLICATIONS

This application is a Continuation-in-Part of U.S. patent application Ser. No. 10/347,553 filed Jan. 21, 2003, now abandoned.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

There has been voluminous research conducted on the biochemistry of injury and disease conditions. Conversely, there has been little or no research directed at possible adverse reactions to inhaled atmospheric gases. Specifically, outside of its known potential for adverse reactions in deep sea diving, no knowledge has been developed about any undesirable reactions to inhaled nitrogen. Based on the research of the inventor it becomes clear that gases other than oxygen can enter and fill mitochondria, and since these gases are not usable for oxidative metabolism, they might be expected to interfere with the production of ATP and therein compromise mitochondrial membrane integrity.

Whereas this phenomenon might be expected with volatile anesthetics, what is added by this specification is the very real potential danger from constantly inhaled atmospheric nitrogen gas in selected injury and disease conditions.

BRIEF SUMMARY OF THE INVENTION

In certain conditions wherein blood flow may be minimally compromised or completely occluded for a period of time, the supply of oxygen to the affected tissue is decreased to a degree that some of the mitochondria in the immediate region are inadequately oxygenated. In this case, oxidative metabolism will be impaired, perhaps to a degree that mitochondrial membrane integrity is compromised and nitrogen begins to leak in and fill the intramitochondrial space. Mitochondria filled with nitrogen are unable to carry on aerobic metabolism and will develop acidosis, followed by cell death. If full reperfusion of the tissues is accomplished, one might expect the problem to reverse itself. However, since the body water of a living animal is completely saturated with nitrogen from inhaled atmospheric gases, there is no possibility for a rapid gradient reversal and washout of nitrogen from these oxygen-compromised mitochondria, so the affected tissues may proceed to cell death and necrosis. The only way in which to circumvent this problem of gas physics is to purge or washout the nitrogen from the body tissues, including the mitochondria, so that oxygen can re-gain access to the interior of affected mitochondria. The scenario then becomes a simple matter of eliminating nitrogen from the inhaled gas mixtures and replacing it with a gas or gases which will facilitate nitrogen washout. A major total body lowering of the nitrogen gas tension in normally perfused tissues will, once reperfusion is achieved, permit a rapid reverse-gradient washout of nitrogen from the ischemic tissues and mitochondria. This invention describes procedures and suitable gas mixtures for use in this regard. The use of oxygen or oxygen-helium gas mixtures, when inhaled as soon as possible after the onset of a stroke or heart attack, can be used to effect a washout of nitrogen from the body to a degree that when reperfusion is established, nitrogen will be cleared from the ischemic tissues and oxidative metabolism will return. It is expected that the clinical benefit will be a significant reduction in reperfusion damage and cell death in the ischemic regions of strokes and heart attacks. The gas formulations for these uses would include helium and oxygen at ranges of 0-80% and 20-100% respectively. For purposes of this disclosure, the terms nitrogen, oxygen and helium used herein shall mean the molecular gas forms of these chemical elements.

DETAILED DESCRIPTION OF THE INVENTION

Nitrogen is a gas which comprises 79% of the air which is breathed by all animals. The possibility of asphyxiation from nitrogen has been long appreciated, but it has not been considered a problem so long as the inhaled oxygen concentration is 20% or higher. Although nitrogen is generally a benign carrier gas, there are conditions wherein it can become very toxic even in the presence of normal or elevated (20-100%) concentrations of inhaled oxygen. In those instances where nitrogen enters and partially or completely fills the intramitochondrial space, it can physically block oxygen uptake leading to anaerobic metabolism, acidosis and cell death. In clinical medicine there are some specific conditions in which nitrogen toxicity becomes a problem when blood flow to specific organs or tissues is blocked, i.e. cerebrovascular accidents (strokes), or myocardial infarction (heart attacks), among others. Following these incidents, mitochondria in the blood flow compromised regions continue to utilize oxygen from the immediate aqueous environment, but when that supply is exhausted, the affected mitochondria cease oxidative metabolism leading to a reduction in the production of ATP and a breakdown of mitochondrial membrane integrity. At this point nitrogen begins to leak into and fill the mitochondria. A subsequent replenishment of blood flow is often less than successful in providing full re-oxygenation and metabolic recovery to the tissue, because that nitrogen entrapped within in the mitochondria physically blocks the re-entry of oxygen. This may explain a phenomenon known as "luxury-perfusion", wherein the tissues sometimes fail to recover following reperfusion even though bathed by an apparent excess of blood and oxygen. The need for improved medical therapy for strokes and heart attacks is clear. It is this inventors carefully studied scientific conclusion, that strokes and heart attacks can be favorably treated by employing various gas formulations for inhalation which can foster the washout of nitrogen from the body and mitochondria, allow the re-entry of oxygen into mitochondria, and re-establish oxidative metabolism. The number of effective formulations might be many, but for the purposes of this invention would be limited to oxygen or gas mixtures of helium and oxygen. Any gas formulation which has as its main purpose the washout of nitrogen from the body would surely be devoid of nitrogen per se. Oxygen would be a requisite gas, and could be used at 100%, but that might not foster the fastest washout of nitrogen from the body or mitochondria. The oxygen content of the inhaled gas mixtures would be established at a range of about 20-100%. Helium is very desirable because of its low density. Indeed, it has been used in conjunction with oxygen as a gas mixture (Heliox) which promotes ease of breathing for patients with impaired respiratory function. Helium could find high penetrability into mitochondria and facilitate the washout of nitrogen. However, helium is expensive and its low (~1%) solubility would only require about 700 ml for saturation of the body water. Therefore, helium would be employed at concentrations as low as 0% ranging up to 80%, i.e. complementary to that of oxygen to achieve the total of 100%. The specific concentrations of the two gases within the ranges specified above would not be as important as the exclusion of nitrogen from the mixture and the specific nitrogen washout technique described below. In practical clinical use, an optimized mixture of oxygen and helium would be inhaled from a suitable gas delivery system such as premixed tanks, tanks with mixing valves or hospital gas supply lines, and exhaled gases would be shunted to ambient atmosphere through a one-way flutter valve. Typically the heart attack or stroke patient would start breathing in an optimized oxygen-helium mixture with exhaled gases shunted to the ambient atmosphere to force the washout of nitrogen from the body water.

This nitrogen gas washout technique could be started during patient transport or upon admission to the hospital. Nitrogen would be washed out of the body at a rate of about 18 ml per minute so that about half (50%) of the body nitrogen would be exhaled during the first half hour. This washout estimate is based on pro formal calculations of about 70 liters of body water and a ~1.5% water solubility for nitrogen, which calculates to 1,050 ml as the saturated total body water capacity for nitrogen; and 18 ml for 30 minutes calculates to 540 ml, i.e. about half of the total body water nitrogen. If 50% can be projected as the minimum percentage washout which would provide any significant clinical benefit, improved clinical results might be expected from nitrogen washouts of 75-90% or more and this could require washout periods of 60 to 90 minutes or longer. If, at these or some delayed time frames, blood flow is re-established to the ischemic tissues, there would exist a higher concentration of nitrogen in the water and mitochondria of the ischemic region than in the surrounding tissues which had been undergoing nitrogen washout. As a result, a reverse partial pressure gradient for nitrogen would exist which would promote the removal of nitrogen from the ischemic region tissues back into the circulating blood and to the lungs for exhalation. This reverse gradient would also extend to that nitrogen trapped in the mitochondria, and it would be expected that the small molecule of helium would easily gain access to the interior of the affected mitochondria to further hasten the nitrogen washout. Along with helium, oxygen would then regain access into mitochondria, returning said mitochondria to a state of oxidative metabolism with a concurrent return of mitochondrial membrane integrity and selectivity.

In practice, the patient would continue to breathe that gas mixture from 30 minutes minimum up to about 72 hours depending on the severity and duration of the original vascular blockage. The extended time frame beyond 1-2 hours for inhaling the gas mixture and continuing nitrogen washout may be a clinical decision to ensure that mitochondrial metabolism and mitochondrial membrane repair, function and stability have been fully restored to levels wherein the reintroduction of high concentrations of inhaled nitrogen would not re-aggravate the ischemic injury.

Clearly in the scope of the invention, i.e. the washout of nitrogen from the body and mitochondria, there are many gas mixtures which might be contemplated and which should be considered as being anticipated by this disclosure. However, for the purposes of the specific uses mentioned above, the exhalation-facilitated nitrogen washout process per se is paramount, and the favored gas mixtures need only contain oxygen, but most favorably, also helium.

The hardware, gas cylinder, gas mixing technology, one-way gas flutter valves and other ancillary equipment required to practice this invention are known in the art and are not part of this invention. Multiple systems could prove useful at various stages of the nitrogen washout process. The most effective would employ a face mask inhalation device with a one-way flutter valve to shunt exhaled gases into ambient atmosphere. Less effective systems, but suitable for longer periods of slower nitrogen washout or for maintenance of low concentrations of inhaled nitrogen would be bed tents or drapes with exit ports for exhaled gases, wherein some re-breathing of exhaled nitrogen would be expected. As well, nasal cannula tubing systems could be employed, but these would be open to some inhaled gas nitrogen contamination from room air. When and how best to employ the various equipment options would be determined over time through clinical use experience. This invention is restricted to the use of certain limited gas mixtures as a means of medical therapy to reverse nitrogen accumulation from normal and ischemic tissues and, in particular, from mitochondria.

What I claim as my invention is:

1. A process for treating reversible blood vessel occlusions in a human being who has suffered an ischemic cerebrovascular accident (stroke) by reversing the trapping of nitrogen by hypoxic mitochondria that causes an impairment in oxidative metabolism in said mitochondria of stroke-affected tissues, which comprises administering through a face mask the inhalation of a nitrogen free gas mixture of oxygen and helium, each at a 20-80% complementary concentrations with exhalations being shunted through a one-way flutter valve into the ambient atmosphere thereby effecting a nitrogen washout from the body of about 18 ml per minute resulting in a 50-90% washout of nitrogen from the body and body water within 30-90 minutes and with slightly longer times for near-total washout, said washout continuing until and beyond the time that blood flow is restored to the stroke-affected compromised tissues to permit a secondary reverse-gradient washout of nitrogen from said tissues and said hypoxic mitochondria thereby allowing the mitochondria of said tissues to re-access oxygen and return to a state of oxidative metabolism.

2. The process of claim 1 where the treatment is implemented as soon as possible following admission to the hospital and continued for 30 minutes up to 72 hours to assure optimum therapy and minimize cell death.

3. The process of claim 2 wherein the gas mixture is 30% oxygen and 70% helium.

4. The process of claim 1 wherein the gas mixture is 30% oxygen and 70% helium.

* * * * *